(12) United States Patent
Brennan, III

(10) Patent No.: US 7,952,719 B2
(45) Date of Patent: May 31, 2011

(54) OPTICAL CATHETER CONFIGURATIONS COMBINING RAMAN SPECTROSCOPY WITH OPTICAL FIBER-BASED LOW COHERENCE REFLECTOMETRY

(75) Inventor: James F. Brennan, III, Matthews, NC (US)

(73) Assignee: Prescient Medical, Inc., Doylestown, PA (US)

( * ) Notice: Subject to any disclaimer, the term of this patent is extended or adjusted under 35 U.S.C. 154(b) by 242 days.

(21) Appl. No.: 12/135,185

(22) Filed: Jun. 8, 2008

(65) Prior Publication Data

US 2008/0304074 A1   Dec. 11, 2008

Related U.S. Application Data

(60) Provisional application No. 60/929,020, filed on Jun. 8, 2007.

(51) Int. Cl.
*G01B 9/02* (2006.01)
*G01N 21/00* (2006.01)

(52) U.S. Cl. .......................................... 356/479; 356/73
(58) Field of Classification Search .................. 356/479, 356/497, 451, 454, 456, 477
See application file for complete search history.

(56) References Cited

U.S. PATENT DOCUMENTS

| | | | |
|---|---|---|---|
| 4,508,524 A | 4/1985 | Romagnoli | |
| 4,530,569 A | 7/1985 | Squire | |
| 4,913,142 A | 4/1990 | Kittrell et al. | |
| 4,976,710 A | 12/1990 | Mackin | |
| 5,076,659 A | 12/1991 | Bekiarian et al. | |
| 5,112,127 A | 5/1992 | Carrabba et al. | |
| 5,139,334 A | 8/1992 | Clarke | |
| 5,166,756 A | 11/1992 | McGee et al. | |
| 5,199,431 A | 4/1993 | Kittrell et al. | |
| 5,217,456 A | 6/1993 | Narciso, Jr. | |
| 5,275,594 A | 1/1994 | Baker et al. | |
| 5,280,788 A | 1/1994 | Janes et al. | |
| 5,293,872 A | 3/1994 | Alfano et al. | |
| 5,321,501 A * | 6/1994 | Swanson et al. .............. 356/479 |
| 5,395,361 A | 3/1995 | Fox et al. | |
| 5,409,483 A | 4/1995 | Campbell et al. | |
| 5,415,654 A | 5/1995 | Daikuzono | |
| 5,439,000 A | 8/1995 | Gunderson et al. | |
| 5,452,723 A | 9/1995 | Wu et al. | |
| 5,455,673 A | 10/1995 | Alsmeyer et al. | |

(Continued)

FOREIGN PATENT DOCUMENTS

WO   WO-2004-051242   6/2004

(Continued)

OTHER PUBLICATIONS

International Search Report and Written Opinion for PCT/US08/66231, mailed Aug. 22, 2008.

(Continued)

*Primary Examiner* — Gregory J Toatley
*Assistant Examiner* — Scott M Richey
(74) *Attorney, Agent, or Firm* — Patton Boggs LLP

(57) ABSTRACT

The present invention provides apparatuses and methods for sample analysis, such as tissue analysis, that integrate high wavenumber (HW) Raman spectroscopy for chemical composition analysis and optical coherence tomography (OCT) to provide depth and morphological information. The invention also provides side-viewing optical probes that are based on a single double clad optical fiber for performing the combined HW Raman spectroscopy and OCT. Intravascular catheter embodiments and related vascular diagnostic methods are also provided.

34 Claims, 6 Drawing Sheets

U.S. PATENT DOCUMENTS

| | | | |
|---|---|---|---|
| 5,459,570 A * | 10/1995 | Swanson et al. | 356/479 |
| 5,479,543 A | 12/1995 | Black | |
| 5,582,170 A | 12/1996 | Soller | |
| 5,615,673 A | 4/1997 | Berger et al. | |
| 5,764,823 A | 6/1998 | Shapanus et al. | |
| 5,773,835 A | 6/1998 | Sinofsky | |
| 5,835,649 A | 11/1998 | Turner et al. | |
| 5,838,700 A | 11/1998 | Dianov et al. | |
| 5,840,023 A | 11/1998 | Oraevsky et al. | |
| 5,842,995 A | 12/1998 | Mahadevan-Jansen et al. | |
| 5,851,980 A | 12/1998 | Avery | |
| 5,861,980 A | 1/1999 | Ono | |
| 5,871,449 A | 2/1999 | Brown | |
| 5,902,246 A | 5/1999 | McHenry et al. | |
| 5,902,247 A | 5/1999 | Coe et al. | |
| 5,951,482 A | 9/1999 | Winston et al. | |
| 5,953,477 A | 9/1999 | Wach et al. | |
| 5,993,378 A | 11/1999 | Lemelson | |
| 6,002,480 A * | 12/1999 | Izatt et al. | 356/479 |
| 6,004,271 A | 12/1999 | Moore | |
| 6,134,003 A | 10/2000 | Tearney et al. | |
| 6,144,791 A | 11/2000 | Wach et al. | |
| 6,208,887 B1 | 3/2001 | Clarke | |
| 6,212,308 B1 | 4/2001 | Donald | |
| 6,222,970 B1 | 4/2001 | Wach et al. | |
| 6,272,376 B1 | 8/2001 | Marcu et al. | |
| 6,277,077 B1 | 8/2001 | Brisken et al. | |
| 6,281,976 B1 | 8/2001 | Taylor et al. | |
| H2002 H | 11/2001 | McLachlan et al. | |
| 6,353,476 B1 | 3/2002 | Allen et al. | |
| 6,366,726 B1 | 4/2002 | Wach et al. | |
| 6,370,306 B1 | 4/2002 | Sato et al. | |
| 6,384,915 B1 | 5/2002 | Everett et al. | |
| 6,389,307 B1 | 5/2002 | Abela | |
| 6,396,976 B1 | 5/2002 | Little et al. | |
| 6,445,939 B1 | 9/2002 | Swanson et al. | |
| 6,450,971 B1 | 9/2002 | Andrus et al. | |
| 6,463,313 B1 | 10/2002 | Winston et al. | |
| 6,475,210 B1 | 11/2002 | Phelps et al. | |
| 6,485,413 B1 * | 11/2002 | Boppart et al. | 600/160 |
| 6,501,551 B1 | 12/2002 | Tearney et al. | |
| 6,506,144 B1 | 1/2003 | Gilan et al. | |
| 6,507,747 B1 | 1/2003 | Gowda et al. | |
| 6,514,214 B2 | 2/2003 | Kokate et al. | |
| 6,522,913 B2 | 2/2003 | Swanson et al. | |
| 6,575,623 B2 | 6/2003 | Werneth | |
| 6,577,891 B1 | 6/2003 | Jaross et al. | |
| 6,597,000 B2 | 7/2003 | Stern | |
| 6,615,063 B1 | 9/2003 | Ntziachristos et al. | |
| 6,659,956 B2 | 12/2003 | Barzell et al. | |
| 6,673,066 B2 | 1/2004 | Werneth | |
| 6,675,106 B1 | 1/2004 | Keenan et al. | |
| 6,690,966 B1 | 2/2004 | Rava et al. | |
| 6,694,181 B2 | 2/2004 | Kokate et al. | |
| 6,701,181 B2 | 3/2004 | Tang et al. | |
| 6,706,004 B2 | 3/2004 | Tearney et al. | |
| 6,813,401 B1 | 11/2004 | Mills et al. | |
| 6,814,727 B2 | 11/2004 | Mansouri-Ruiz | |
| 6,816,743 B2 | 11/2004 | Moreno et al. | |
| 6,839,496 B1 | 1/2005 | Mills et al. | |
| 6,860,851 B2 | 3/2005 | Knudson et al. | |
| 6,873,868 B2 | 3/2005 | Furnish | |
| 6,903,854 B2 | 6/2005 | Gelikonov et al. | |
| 6,904,199 B2 | 6/2005 | Zuluaga | |
| 6,906,050 B2 | 6/2005 | Robinson | |
| 6,922,498 B2 | 7/2005 | Shah | |
| 6,949,072 B2 | 9/2005 | Furnish et al. | |
| 6,974,465 B2 | 12/2005 | Belef et al. | |
| 7,004,911 B1 | 2/2006 | Tu et al. | |
| 7,039,452 B2 | 5/2006 | McClane et al. | |
| 7,050,672 B1 | 5/2006 | Matsumoto et al. | |
| 7,061,606 B2 | 6/2006 | Treado et al. | |
| 7,123,968 B1 | 10/2006 | Casscells, III et al. | |
| 7,153,299 B1 | 12/2006 | Tu et al. | |
| 7,177,491 B2 | 2/2007 | Dave et al. | |
| 7,190,464 B2 | 3/2007 | Alphonse | |
| 7,313,432 B2 | 12/2007 | Tearney | |
| 7,355,716 B2 * | 4/2008 | de Boer et al. | 356/479 |
| 7,414,729 B2 * | 8/2008 | Xie et al. | 356/484 |
| 7,418,169 B2 * | 8/2008 | Tearney et al. | 385/25 |
| 7,447,408 B2 * | 11/2008 | Bouma et al. | 385/123 |
| 7,499,153 B2 * | 3/2009 | Puppels et al. | 356/73 |
| 7,508,524 B2 * | 3/2009 | Mahadevan-Jansen et al. | 356/479 |
| 7,538,859 B2 * | 5/2009 | Tearney et al. | 356/35.5 |
| 7,539,363 B2 | 5/2009 | Bock et al. | |
| 7,593,763 B2 * | 9/2009 | Lambert et al. | 600/476 |
| 2001/0012429 A1 | 8/2001 | Wach et al. | |
| 2001/0047137 A1 | 11/2001 | Moreno et al. | |
| 2002/0071474 A1 | 6/2002 | Werneth | |
| 2002/0071647 A1 * | 6/2002 | Manzur | 385/127 |
| 2002/0183601 A1 | 12/2002 | Tearney et al. | |
| 2002/0183620 A1 | 12/2002 | Tearney et al. | |
| 2002/0183622 A1 | 12/2002 | Zuluaga et al. | |
| 2002/0193735 A1 | 12/2002 | Stiger | |
| 2003/0032204 A1 | 2/2003 | Walt et al. | |
| 2003/0032880 A1 | 2/2003 | Moore | |
| 2003/0047608 A1 | 3/2003 | Huss et al. | |
| 2003/0125630 A1 | 7/2003 | Furnish | |
| 2003/0199747 A1 | 10/2003 | Michlitsch et al. | |
| 2003/0199767 A1 | 10/2003 | Cespedes et al. | |
| 2003/0199768 A1 | 10/2003 | Cespedes et al. | |
| 2003/0236443 A1 | 12/2003 | Cespedes et al. | |
| 2004/0073120 A1 | 4/2004 | Motz et al. | |
| 2004/0077950 A1 | 4/2004 | Marshik-Geurts et al. | |
| 2004/0093044 A1 | 5/2004 | Rychnovsky et al. | |
| 2004/0111016 A1 | 6/2004 | Casscells, III et al. | |
| 2004/0176699 A1 | 9/2004 | Walker et al. | |
| 2004/0204651 A1 | 10/2004 | Freeman et al. | |
| 2004/0260182 A1 | 12/2004 | Zuluaga et al. | |
| 2004/0260183 A1 * | 12/2004 | Lambert et al. | 600/476 |
| 2004/0267110 A1 | 12/2004 | Tremble | |
| 2005/0020925 A1 | 1/2005 | Kleen et al. | |
| 2005/0054934 A1 | 3/2005 | Furnish et al. | |
| 2005/0075574 A1 | 4/2005 | Furnish et al. | |
| 2005/0075704 A1 | 4/2005 | Tu et al. | |
| 2005/0080402 A1 | 4/2005 | Santamore et al. | |
| 2005/0096647 A1 | 5/2005 | Steinke et al. | |
| 2005/0107706 A1 | 5/2005 | Zuluaga et al. | |
| 2005/0165315 A1 | 7/2005 | Zuluaga et al. | |
| 2005/0283058 A1 * | 12/2005 | Choo-Smith et al. | 600/315 |
| 2005/0288564 A1 | 12/2005 | Iuliano | |
| 2006/0013544 A1 * | 1/2006 | Bouma et al. | 385/116 |
| 2006/0058622 A1 | 3/2006 | Tearney et al. | |
| 2006/0100190 A1 | 5/2006 | Cheong et al. | |
| 2006/0139633 A1 | 6/2006 | Puppels et al. | |
| 2006/0146322 A1 | 7/2006 | Komachi et al. | |
| 2006/0184232 A1 | 8/2006 | Gianotti et al. | |
| 2007/0016054 A1 | 1/2007 | Cao et al. | |
| 2007/0032814 A1 | 2/2007 | Hibler | |
| 2007/0076212 A1 | 4/2007 | Zuluaga | |
| 2007/0081166 A1 * | 4/2007 | Brown et al. | 356/479 |
| 2007/0087445 A1 | 4/2007 | Tearney et al. | |
| 2007/0208257 A1 | 9/2007 | Furnish | |
| 2007/0219451 A1 | 9/2007 | Kula et al. | |
| 2007/0238953 A1 | 10/2007 | Lucassen et al. | |
| 2007/0265602 A1 | 11/2007 | Mordaunt et al. | |
| 2008/0002927 A1 | 1/2008 | Furnish | |
| 2008/0007716 A1 * | 1/2008 | Igarashi | 356/72 |
| 2008/0129993 A1 | 6/2008 | Brennan et al. | |
| 2008/0177139 A1 | 7/2008 | Courtney et al. | |
| 2008/0304074 A1 | 12/2008 | Brennan, III | |
| 2009/0003765 A1 * | 1/2009 | Bouma et al. | 385/14 |
| 2009/0003789 A1 * | 1/2009 | Bouma et al. | 385/126 |
| 2009/0022463 A1 * | 1/2009 | Bouma et al. | 385/126 |
| 2010/0045778 A1 * | 2/2010 | Yelin | 348/45 |

FOREIGN PATENT DOCUMENTS

| | | |
|---|---|---|
| WO | WO-2005-019800 | 3/2005 |
| WO | WO-2005-069838 | 8/2005 |
| WO | WO-2007-032814 | 3/2007 |
| WO | WO-2007-103235 | 9/2007 |
| WO | WO-2007-146254 | 12/2007 |
| WO | WO-2008-011163 | 1/2008 |
| WO | WO-2008-051950 | 5/2008 |
| WO | WO-2008-144600 | 11/2008 |
| WO | WO-2008-154460 | 12/2008 |

| WO | WO-2009-011873 | 1/2009 |
| WO | WO-2009-014820 | 1/2009 |
| WO | WO-2009-038555 | 3/2009 |
| WO | WO-2009-140608 | 11/2009 |
| WO | WO-2010-144714 | 12/2010 |

OTHER PUBLICATIONS

Mahadevan-Jansen et al., "Combined raman spectroscopy-optical coherence tomography (rs-oct) system and applications of the same," *OCT News*, 2009, 1 page. http://www.octnews.org/articles/1012630/. Accessed Jan. 10, 2001.

Brennan et al., "Near-Infrared Raman Spectrometer Systems for Human Tissue Studies," *Applied Spectroscopy*, 1997: 51(2), pp. 201-208.

Römer et al., "Histopathology of Human Coronary Atherosclerosi Quantifying Its Chemical Composition With Raman Spectroscopy," *American Heart Association, Inc.*, 1998, pp. 879-885.

Utzinger et al., "Fiber Optical probes for Biomedical Optical Spectroscopy," *J. Biomed*, 2003: 8, pp. 121-147.

Edwards et al., "Potential Applications of FT-Raman Spectroscopy for Dermatological Diagnostics," *J. Mol. Struc.*, 1995: 347, pp. 379-388.

Komachi et al., "Micro-optical fiber probe for use in an intravascular Raman endoscope," *Applied Optics*, 2005: 44(22), pp. 4722-4732, espcially: p. 4726, col. 2.

* cited by examiner

OPTICAL CATHETER CONFIGURATIONS COMBINING RAMAN SPECTROSCOPY WITH OPTICAL FIBER-BASED LOW COHERENCE REFLECTOMETRY

FIELD OF THE INVENTION

This application claims the benefit of U.S. provisional application Ser. No. 60/929,020 filed Jun. 8, 2007, which is incorporated by reference herein in its entirety.

FIELD OF THE INVENTION

The invention relates to the field of catheter-based optical diagnostic probes and more specifically to fiber optic probes for performing Raman spectroscopy and optical coherence tomography.

BACKGROUND OF INVENTION

Catheter-based Raman spectroscopy has been previously proposed for the chemical analysis and diagnosis of vascular tissue including human atherosclerotic lesions. However, typical methods of collecting Raman scattered light from the surfaces of artery do not register information about the distance of the scattering element from the collection optics. Raman spectroscopy techniques that do incorporate optical methodologies for depth-sensing information have been too large to be incorporated into intravascular catheters. One method previously explored by one of the inventors (Brennan) involved a combination IVUS/Raman catheter for intravascular diagnosis. These prior studies focused on using the Raman-scattered light in the Raman "fingerprint" region to supplement the IVUS data. The collection of Raman spectra in the fingerprint (FP) region, i.e., approximately 200 to 2,000 $cm^{-1}$, through optical fibers is complicated by Raman signal from the fibers themselves. In order to collect uncorrupted FP spectra, it has been necessary to incorporate complex optics and filters on the tips of catheters and often these designs require the use of multiple optical fibers. Since the Raman-scattered signal is weak, large multimode fibers are utilized in the multi-fiber catheter designs resulting in an unwieldy catheter that is generally incapable of exploring delicate arteries, such as the human coronary arteries.

U.S. Pat. No. 5,953,477 discloses methods and apparatuses for the manipulation and management of fiber optic light, and is incorporated by reference herein in its entirety.

U.S. Pat. No. 6,144,791 discloses the use of beam steering techniques in optical probes, and is incorporated by reference herein in its entirety.

U.S. Pat. No. 6,222,970 discloses methods and apparatuses for filtering optical fibers and applying filters to optical fibers, and is incorporated by reference herein in its entirety.

U.S. Pat. No. 6,445,939 discloses ultra-small optical probes, imaging optics and methods of using the same, and is incorporated by reference herein in its entirety.

U.S. Pat. No. 6,507,747 discloses optical imaging probes that include a spectroscopic imaging element and an optical coherence tomography imaging element, and is incorporated by reference herein in its entirety.

U.S. Pat. No. 6,904,199 discloses optical catheters that include a double clad optical fiber, and is incorporated by reference herein in its entirety.

U.S. Pat. No. 7,177,491 discloses optical fiber-based optical low coherence tomography, and is incorporated by reference herein in its entirety.

U.S. Pat. No. 7,190,464 discloses low coherence interferometry for the detection and characterization of atherosclerotic vascular tissue, and is incorporated by reference herein in its entirety.

U.S. Publication No. 2001/0047137 discloses the use of near-infrared spectroscopy for the characterization of vascular tissue and teaches against the use of Raman spectroscopy for such characterization, and is incorporated by reference herein in its entirety.

U.S. Publication No. 2004/0260182 discloses intraluminal spectroscope devices with wall-contacting probes, and is incorporated by reference herein in its entirety.

U.S. Publication No. 2005/0054934 discloses an optical catheter with dual-stage beam redirector, and is incorporated by reference herein in its entirety.

U.S. Publication No. 2006/0139633 discloses the use of high wavenumber Raman spectroscopy for the characterization of tissue, and is incorporated by reference herein in its entirety. Santos et al., *Fiber-Optic Probes for In Vivo Raman Spectroscopy in the High-Wavenumber Region*, Anal. Chem. 2005, 77, 6747-6752 discloses probe designs for high wavenumber Raman spectroscopy, and is incorporated by reference herein in its entirety.

U.S. Publication No. 2007/0076212 discloses catheter-based methods and apparatuses for analyzing vascular tissue that combine infrared spectroscopy for chemical analysis with optical coherence tomography, and is incorporated by reference herein in its entirety.

U.S. Publication No. 2004/0260182 discloses intraluminal spectroscope devices with wall-contacting probes, and is incorporated by reference herein in its entirety.

U.S. Publication No. 2005/0054934 discloses an optical catheter with dual-stage beam redirector, and is incorporated by reference herein in its entirety.

In view of the above, what is needed is a single optical fiber-based optical probe design that enables catheter-based Raman spectroscopy and optical coherence tomography and methods of diagnosing tissue using the same.

SUMMARY OF INVENTION

The invention provides apparatuses, systems and methods for performing both high wavenumber Raman spectroscopy and optical coherence tomography over a single double clad optical fiber, in order to obtain chemical composition information and depth/morphological information about the same tissue target.

One embodiment of the invention provides a fiber optic probe system (apparatus) capable of performing high wavenumber Raman spectroscopy and optical coherence tomography over an optical fiber that includes:

a double clad optical fiber having a proximal end, a distal probe end and a central longitudinal axis and comprising a core, an inner clad surrounding the core and an outer clad surrounding the inner clad;

a laser light source operably coupled or selectively operably coupleable to the proximal end of the double clad fiber to transmit excitation light down the core and/or the inner clad of the double clad fiber;

an interferometry light source operably coupled or selectively operably coupleable to the proximal end of the double clad fiber to transmit light down the core of the double clad fiber in the performance of interferometry by the system;

a Raman spectrometer operably coupled or selectively operably coupleable to the proximal end of the double clad fiber to receive Raman scattered light from a sample via the inner clad of the fiber, said spectrometer configured to measure Raman scattered light in the range of 2,500-4,000 cm$^{-1}$; and an interferometer operably coupled or selectively operably coupleable to the proximal end of the double clad fiber to receive phase-shifted light from a sample via the core of the fiber and combine the phase-shifted light with a reference beam.

In one variation, the system includes an optical switch configured to switch between providing illumination by the laser light source for Raman spectroscopy and the interferometry light source for interferometry. In another variation, the system is configured to perform simultaneous Raman spectroscopy and interferometry.

A related embodiment of the invention provides a method for optically analyzing a blood vessel that includes the steps of:

inserting into a blood vessel a double clad optical fiber having a proximal end, a distal probe end and a central longitudinal axis and comprising a core, an inner clad surrounding the core and an outer clad surrounding the inner clad;

launching laser light into the core and/or the inner clad of the double clad fiber at its proximal end to illuminate a tissue region via the distal end of the double clad fiber, thereby generating a Raman spectra from the tissue region;

receiving the Raman spectra via the inner clad of the fiber at the proximal end of the double clad fiber, and measuring the Raman spectra in the range 2,500-4,000 cm$^{-1}$ using a Raman spectrometer configured to measure said range;

launching light from an interferometry light source into the core of the double clad fiber at its proximal end to illuminate the tissue region via the distal end of the double clad fiber, thereby producing a sample beam for interferometric analysis;

receiving the sample beam via the core of the double clad fiber at its proximal end and performing interferometer by combining the sample beam with a reference beam using an interferometer, thereby obtaining both Raman spectroscopic data and interferometric data for the tissue region.

Another embodiment of the invention provides a fiber optic probe system configured to simultaneously perform high wavenumber Raman spectroscopy and optical coherence tomography over an optical fiber:

a double clad optical fiber having a proximal end, a distal probe end and a central longitudinal axis and comprising a core, an inner clad surrounding the core and an outer clad surrounding the inner clad;

a light source operably coupled to the proximal end of the double clad fiber to transmit Raman excitation light down the core and/or the inner clad of the double clad fiber to illuminate a sample with a wavelength range of light;

a Raman spectrometer operably coupled to the proximal end of the double clad fiber to receive Raman scattered light from the sample via the inner clad of the fiber; and an interferometer operably coupled the proximal end of the double clad fiber to receive phase-shifted light from the sample via the core of the fiber and combine the phase-shifted light with a reference beam. The Raman spectrometer may be configured to measure Raman-scattered light in the range of 2,500-4,000 cm$^{-1}$.

A related embodiment of the invention provides a method for optically analyzing a blood vessel that includes the steps of:

inserting into a blood vessel a double clad optical fiber having a proximal end, a distal probe end and a central longitudinal axis and comprising a core, an inner clad surrounding the core and an outer clad surrounding the inner clad;

launching light having a wavelength range into the core and/or the inner clad of the double clad fiber at its proximal end to illuminate a tissue region via the distal end of the double clad fiber, thereby generating both Raman-scattered light from the tissue region and phase shifted light from the tissue region;

receiving the Raman-scattered light via the inner clad of the fiber at the proximal end of the double clad fiber, and measuring the Raman-scattered light using a Raman spectrometer;

receiving the phase-shifted light via the core of the double clad fiber at its proximal end and performing interferometery by combining the phase-shifted with a reference beam using an interferometer, thereby obtaining both Raman spectroscopic data and interferometric data for the tissue region.

The Raman spectrometer may be configured to measure Raman scattered light in the range of 2,500-4,000 cm$^{-1}$.

The optical fibers may be configured for forward or lateral (side) viewing. For example, for lateral-viewing, the distal probe end of the fiber may be angled with respect to the central axis of the fiber to provide off-axis transmission of light and to receive off-axis light. As an alternative, the distal end of the fiber may be operably connected to (in optical communication with) a beam redirecting element such as a miniature prism or mirror face that directs light off-axis and receives off-axis light.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

DETAILED DESCRIPTION

The present invention provides single optical fiber-based optical probe designs that enable catheter-based Raman spectroscopy and optical coherence tomography and methods of diagnosing tissue using the same. Accordingly, the apparatuses and methods of the invention advantageously facilitate the collection of chemical composition information along with depth and/or morphological information.

The present invention enables the integration of high wavenumber (HW) Raman shifted light and optical coherence tomography (OCT) into a single double-clad optical fiber. The use of high wavenumber Raman spectroscopy rather than fingerprint region Raman spectroscopy enables collection of quality Raman spectra via a single optical fiber, such as a multimode fiber with a large core diameter and numerical aperture ("NA") for maximized signal collection. The same fiber is used to perform OCT to obtain depth information about the scattering components and/or information about the physical structure within the examined volume, for example, to discern the morphology of an arterial wall. Low coherence reflectometry through optical fibers, commonly referred to as optical coherence tomography (OCT), can resolve structures with a ~15 um depth resolution and provides complimentary information to that obtained with Raman spectroscopy. OCT is typically performed in the time domain, where light pulses that are spectrally broad are reflected from within a sample volume (see FIG. 1), but the technique can also be readily performed in the frequency domain by sweeping the wavelength of the excitation source or incorporating a spectrometer (see FIGS. 2 and 3), which is commonly referred to as optical frequency domain interferometry (OFDI), frequency domain OCT (FD-OCT), or spectral domain OCT (SD-OCT). A swept single-mode laser light source may be utilized in this case. As used herein, "OCT" refers to and is inclusive of both the time-domain, spectral domain and frequency-domain implementations of low coherence interferometry through optical fibers.

Time Domain OCT

In time domain OCT (TD-OCT), the path length of the reference arm is translated longitudinally in time. A property of low-coherence interferometry is that interference, i.e. the series of dark and bright regions of light (called 'fringes'), is only achieved when the path difference lies within the coherence length of the light source. The envelope of this modulation changes as path length difference is varied, where the peak of the envelope corresponds to path length matching.

Figure 1:
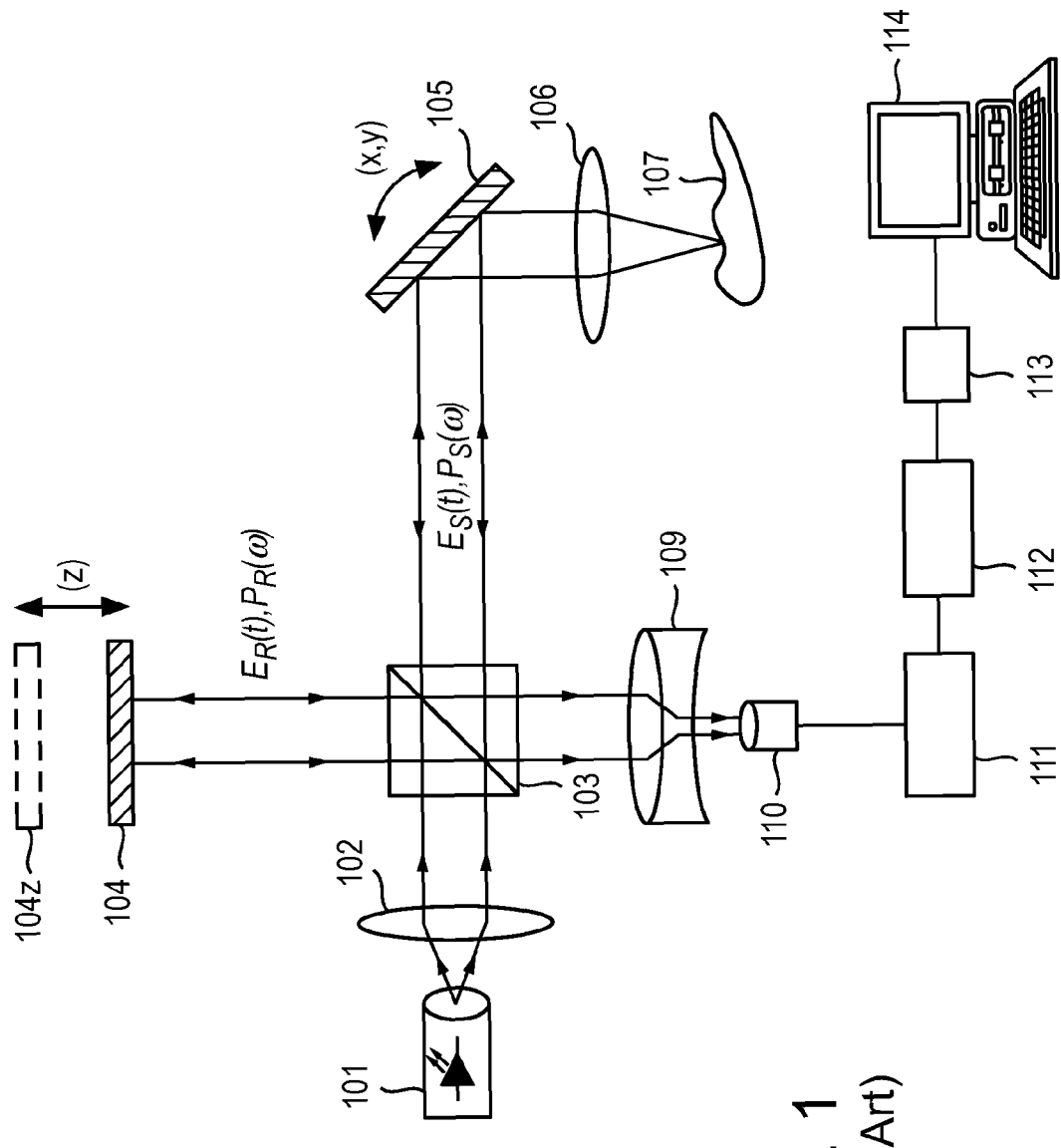
FIG. 1 shows a typical optical setup of single point OCT. Scanning the light beam on the sample enables non-invasive cross-sectional imaging up to 3 mm in depth with micrometer resolution.

FIG. 1 exemplifies a typical optical set-up of a single point TD-OCT system. A low-coherence light source 101 is provided that launches light through a collimator lens 102 toward a beam splitter 103. A portion of the light striking the beam splitter is redirected toward reference mirror 104. Reference mirror 104 may be translated, exemplified by reference mirror position 104z, to provide axial scanning. Another portion of the light entering beam splitter 103 passes through the splitter and strikes mirror 105, which is movable to provide lateral scanning. Light reflected from mirror 105 is directed through an objective lens 106 and thereon to a sample 107 under examination. Light reflected from the sample then takes the reverse path back into beam splitter 103 where it is redirected and combines with light reflected off reference mirror 104. The recombined light then enters beam reducing lens 109, followed by photodetector 110 which converts the light to electronic signals. The electronic signals (analogue) are then processed by a filtering unit 111, followed by a demodulation processing unit 112 and then undergo analog-to-digital (ADC) conversion by an ADC unit. The digital signal is then processed by a computer 114 for processing (e.g., image construction) and storage of data, which also includes a display for displaying gathered OCT images.

Frequency Domain OCT (FD-OCT) and Spectral Domain OCT (SD-OCT)

In frequency domain OCT, the broadband interference is acquired with spectrally separated detectors (e.g., by encoding the optical frequency in time with a spectrally scanning source or with a dispersive detector, like a grating and a linear detector array). Due to the relationship between the auto correlation and the spectral power density, the depth scan can be immediately calculated by a Fourier-transform from the acquired spectra, without movement of the reference arm. This feature improves imaging speed dramatically, while the reduced losses during a single scan improve the signal to noise proportional to the number of detection elements. The parallel detection at multiple wavelength ranges limits the scanning range, while the full spectral bandwidth sets the axial resolution.

Figure 2:
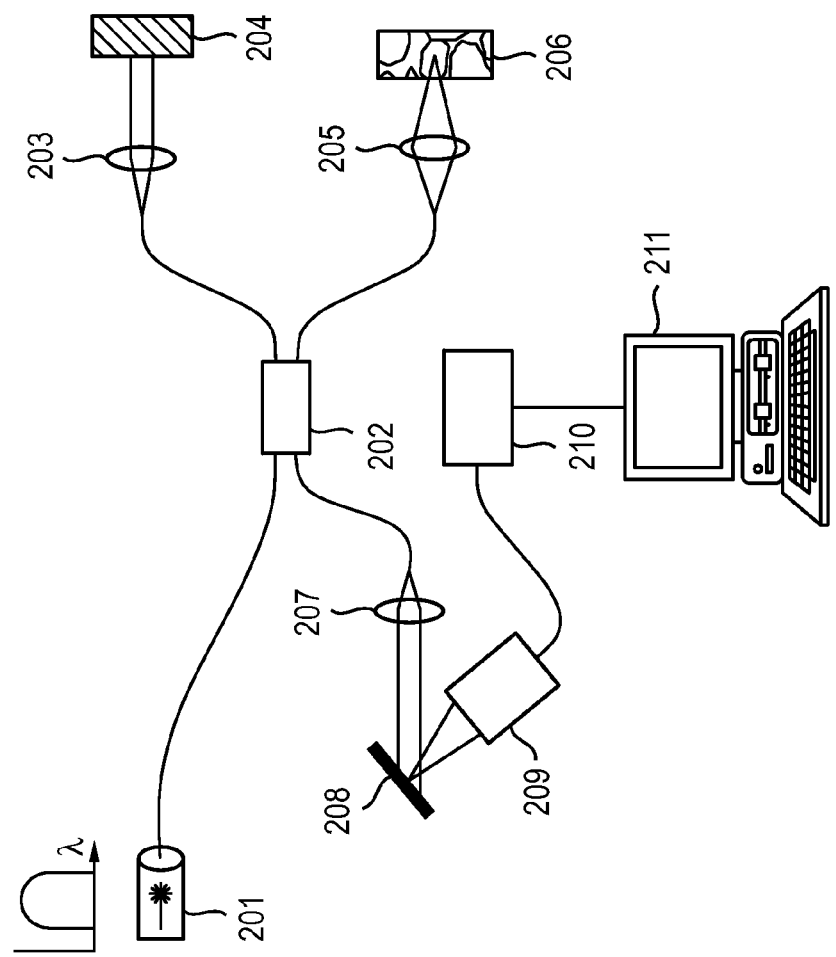
FIG. 2 illustrates spectral discrimination by Fourier-domain OCT. Shown are: low coherence light source, beam splitter, reference mirror, sample, diffraction grating and full-field detector acting as a spectrometer, and digital signal processing unit.

FIG. 2 shows a typical set-up for Fourier-domain OCT. A low-coherence light source 201 is provided that launches light toward and into a dichroic beam splitter 202. A portion of the light is split out toward a reference mirror 204 (first passing collimator lens 203). Another portion of the light passing beam splitter 202 is directed to a sample 206 (first passing an objective lens 205). Light reflected by reference mirror 204 and sample 206 then travel a reverse path back into to beam splitter 202 where they recombine. The recombined light is directed to a collimator lens 207 before striking a diffraction grating 208. Spectrally resolved light from diffraction grating 208 is detected by a full field detector 209, which may be a CCD camera. Full field detector 209 is operably linked to a digital signal processing unit 210 which in turn is operably linked to a computer 221 for processing (e.g., image construction) and storage of data, which also includes a display for displaying gathered OCT images.

Figure 3:
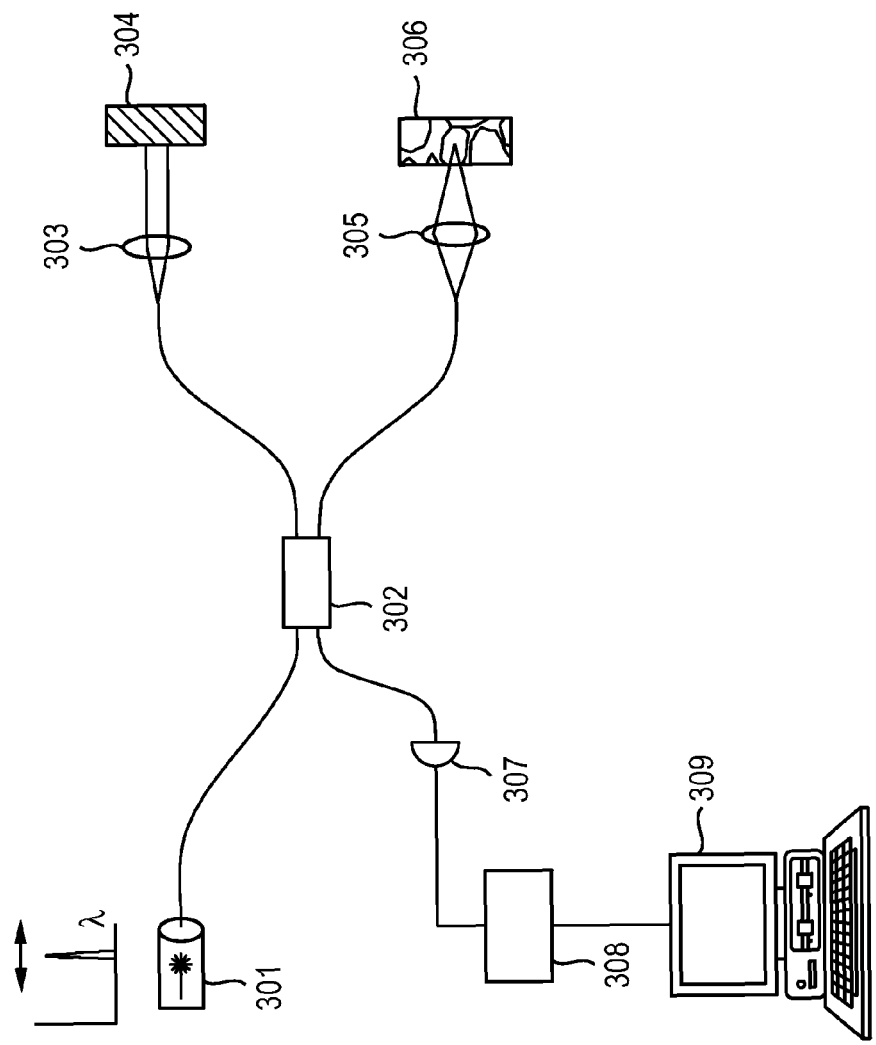
FIG. 3 illustrates spectral discrimination by swept-source OCT. Shown are: swept source or tunable laser, beam splitter reference mirror, sample, photodetector, and digital signal processing unit.

FIG. 3 shows a typical set-up for spectral discrimination by swept-source OCT. A swept source or tunable laser 301 is provided that launches light toward and into a beam splitter 302 from which the light diverges down two separate paths, one path toward reference mirror 304 (first passing collimator lens 303) and the other path toward a sample 306 (first passing objective lens 305). Light reflected by reference mirror 304 and sample 306 then travels a reverse path, recombining in beam splitter 302, before detection by a photodetector 307 which converts detected light into an electronic signal, which is then processed by a digital signal processing unit 308, which provides a digital signal to a computer 309, which performs processing functions (such as image construction), stores data and also includes a display for displaying gathered OCT images.

OCT is an interferometric technique that commonly uses a Michelson interferometer configuration realized with optical fibers. Light pulses are strongly correlated when the arms of the interferometer have equal optical path lengths, therefore the optical fibers used to construct an OCT system are typically single-mode optical fibers, which guide one optical mode and thus provides a controlled optical path length. Multimode fibers allow several (or hundreds) of modes to propagate in the same fibers, tremendously reducing the spatial resolution of an OCT system and creating ambiguities. The optical fiber used in the present invention may be a polarization-maintaining ("PM") optical fiber, which is an optical fiber in which the polarization planes of light waves launched into the fiber are maintained during propagation with little or no cross-coupling of optical power between the polarization modes. A single mode fiber actually supports two modes, i.e. two polarizations. Some current OCT implementations use PM fibers so that a single polarization in a single mode fiber can be used. The double-clad fibers used in the present invention may be engineered as PM fibers by including stress rods, ellipticity, etc., for example, as known in the art. Most PM fibers work by inducing stress in the core via a non-circular cladding cross-section, or via rods of another material included within the cladding. Several different shapes of rod are used in commercially available PM fibers. Background information on PM optical fibers is found, for example, in U.S. Pat. No. 7,050,672, which is incorporated by reference herein in its entirety.

High Wavenumber Raman spectroscopy

One aspect of the invention utilizes Raman scattered light shifted outside of the fingerprint region to conduct tissue analysis, in the high wavenumber (HW) region, i.e., in the range of approximately 2,500-4,000 cm$^{-1}$, for example, in the range 2,500-3,700 cm$^{-1}$ or in the range of 2,600 to 3,200 cm$^{-1}$, and combines this information with OCT data to provide chemical compositional information as a function of depth in a lumen wall, such as a blood vessel wall, such as an artery wall.

Figure 4:
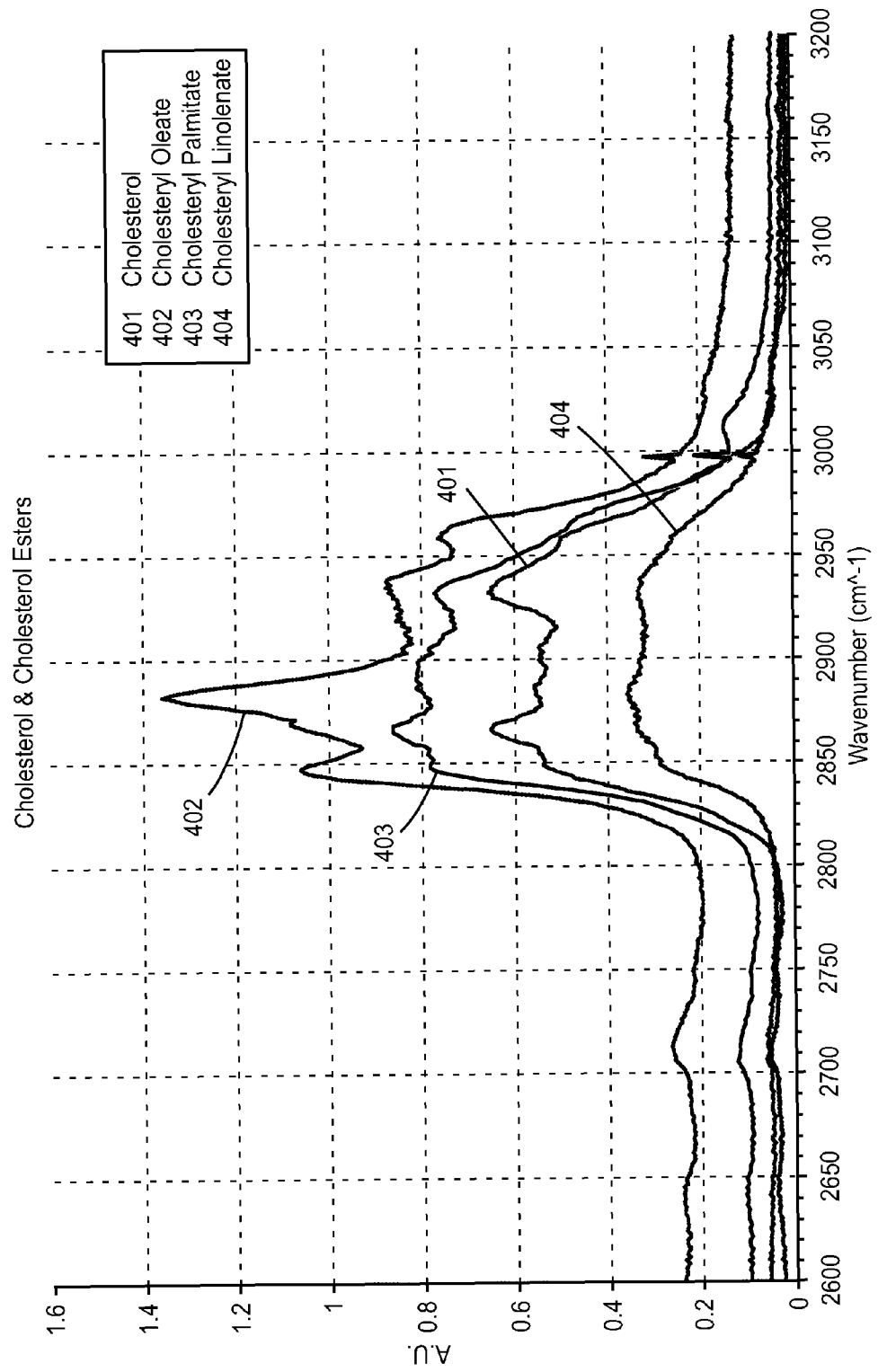
FIG. 4 shows Raman spectra of cholesterol and various cholesterol esters in the Raman high wavenumber region.

Since cholesterol and its esters have distinctive Raman scattering profiles within the Raman high wavenumber region, the use of the Raman high wavenumber region for analysis is particularly useful for locating and characterizing lipid-rich deposits or lesions as may occur in blood vessels, such as atherosclerotic plaques prone to rupture (e.g., so-called vulnerable plaques) in arteries, such as the coronary arteries. FIG. 4 shows Raman spectra of cholesterol and cholesterol esters in the high wavenumber region, which molecules are commonly found in atherosclerotic plaques and lesions. Specifically, curve 401 is a Raman spectrum for cholesterol, curve 402 is a Raman spectrum for cholesteryl oleate, curve 403 is a Raman spectrum for cholesteryl palmitate and curve 404 is a Raman spectrum for cholesteryl linolenate. Thus, in one aspect the invention provides methods for locating and/or characterizing lipid-rich depositions and/or lesions, such as vulnerable plaques, in blood vessel walls such as in arteries, by integrating Raman high wavenumber spectral data to indicate chemical composition and regional depth information from IVUS and/or other depth-sensing capable technology, as described herein.

While OCT systems typically utilize single mode optical fibers, Raman systems employ multimode optical fibers to maximize collection of the weak scattered light signals. The present invention combines the two measurement modalities in a single compact optical fiber sensor employing a double-clad optical fiber to collect both OCT and Raman spectral signals.

Figure 5:
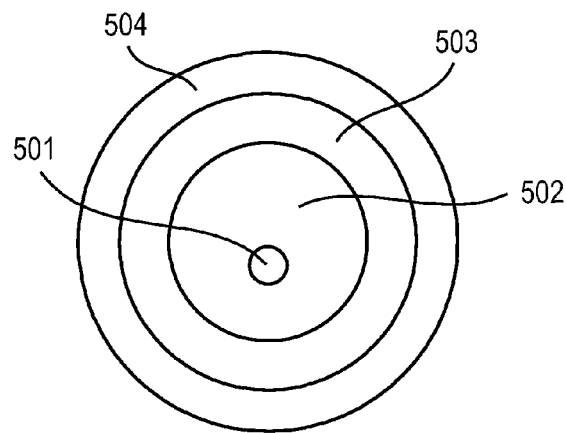
FIG. 5 shows a cross-section of a circular double-clad fiber having an offset core.

Double clad fibers were first introduced in the late 1980s by Snitzer, who proposed to make high power optical amplifiers with the specialty optical fibers. The fibers typically consist of an inner core, which can be single mode, surrounded by a concentric outer core which is multimode. An example of a double clad fiber is shown in FIG. 5. The fiber includes: an innermost "core" 501 which may also be referred to as the "inner core;" an outer core 502 which may also be referred to as the "inner cladding;" an outer cladding 503 surrounding the outer core (surrounding the inner cladding); and, as shown in the figure, an outer jacket layer 504. In optical amplifier applications, the signal to be amplified is introduced in the inner code, while the outer core is high NA and allows maximum coupling of light from pump solid state or semiconductor lasers to be coupled into the fiber and to be eventually absorbed by the inner core amplification medium.

In fiber optics, a double-clad fiber (also "doubly clad" or "dual clad" fiber) is an optical fiber that has a relatively small-diameter core and two layers of cladding. Typically, the relationship between refractive indices of the core and claddings is $n_{core} > n_{inner\,clad} > n_{outer\,clad}$, where "n" in the refractive index. This allows the inner cladding to act as the "core" of a multimode fiber with the outer cladding as its cladding, while the inner core of the double-clad fiber is a true single-mode waveguide.

Double-clad fibers often are used for fiber lasers and optical amplifiers, because the core can be doped to act as the gain medium while the inner cladding layer carries a pump beam used to maintain the population inversion in the core. For such applications, the core may be single-mode or may be multi-mode with a low numerical aperture. The shape of the cladding can be important. Circular symmetry in a double-clad fiber seems to be the worst solution for a fiber laser; in this case, many modes of the light in the cladding miss the core and hence cannot be used to pump it. So-called "chaotic fibers" have more complicated cross-sectional shape and provide more uniform distribution of intensity in the inner cladding, allowing efficient use of the pump light. The so-called "spiral shape" seems to be the most efficient, due to the special behavior of modes in the vicinity of the "chunk" of the spiral domain. Designers of double-clad fiber lasers need to find a reasonable compromise between simple shape (for ease of manufacture) and efficient pumping of the core.

Figure 6:
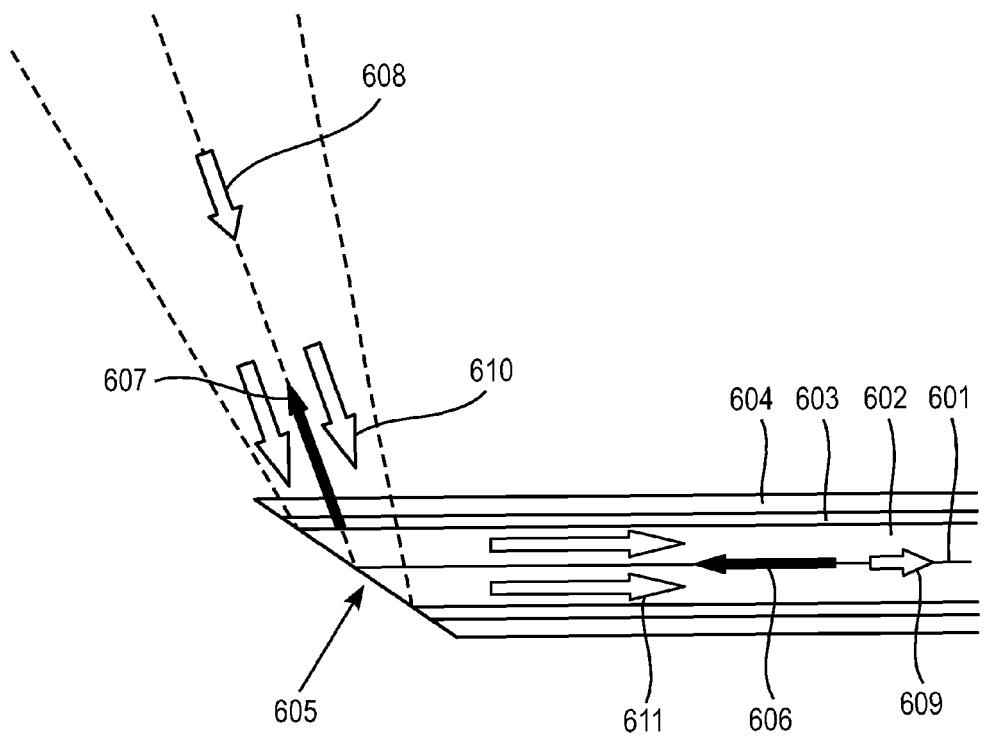
FIG. 6 schematically illustrates a side-viewing high wavenumber Raman optical fiber sensor based on a double-clad fiber with which both OCT and Raman spectroscopy can be performed.

In a combined Raman/OCT sensor application, the OCT signal collection and illumination (for both Raman excitation and OCT) could occur through the inner core of the double-clad fiber, while the outer core (inner clad) will be used to collect Raman scattered light, as shown in FIG. 6.

One embodiment provides for collecting HW Raman-shifted light through the large outer core of the optical fiber. In one variation, the inner core is used to guide the excitation light for the Raman signal generation, and the outer core would be used to collect the resulting scattered light, while the inner core is used for both the OCT signal excitation and collection. In a further variation one or more fiber Bragg gratings are inscribed in the inner fiber core to reduce the amount of background Raman-scattered light from the excitation fiber silica that reaches the sample to be examined. In this particular instance, a frequency-chirped fiber Bragg grating may, for example, be inscribed in the fiber inner core to reflect light that has been Raman scattered by the fiber silica and prevent it from reaching the sample. A grating may be holographically inscribed in the fiber that reflects the Raman shifted light, while allowing the excitation light to pass and enter the sample. In a further variation, the fiber Bragg grating may be a chirped blazed grating (the grating inscribed at an oblique angle to the fiber axis) so that the undesired wavelengths of light are coupled out of the fiber core into radiation modes.

Alternatively, or in addition, the inner clad of the dual clad optical fiber may be used as the guide for excitation light from a Raman spectroscopy light source. In this case, one or more fiber Bragg gratings may be inscribed in the inner clad to reduce the amount of background Raman-scattered light from the excitation fiber silica that propagates in the fiber. Again, the fiber Bragg grating may be a chirped blazed grating (the grating inscribed at an oblique angle to the fiber axis) so that the undesired wavelengths of light are coupled out of the fiber core into radiation modes.

Typical commercially available double-clad fibers are constructed to make high power optical amplifiers, where the inner core is doped with a rare earth ion, such as erbium or erbium/ytterbium, and the outer core (inner clad) is silica. The outermost cladding (outer clad) is typically polymer-based, which allows for a large acceptance NA of pump diode light since the polymer refractive index can be much lower than that of silica. One embodiment of the present invention provides a double clad structure including a "standard" germanium-doped single mode inner core (instead of the typical erbium doped inner layer) and an outer core (inner clad) that is a multimode fiber, such as a typical multimode fiber or one having the characteristics of a typical multimode fiber, such as a 100 um core fiber with a 0.22 NA and a 120 um diameter cladding. A fiber according to this embodiment may be used in any of the methods and systems of the invention.

One method to manufacture these fibers is to use MCVD (modified chemical vapor deposition) to create the inner core in a silica tube (or a tube that has been doped with material such as germanium to raise the refractive index of the overall outer core). The inner core of the fiber may be made by simply creating a region in the fiber center with an increased germanium content, or the confining layer may be made by fabricating refractive index wells by depressing an outer annulus region, for example, by doping with phosphorous and then further depositing layers of higher refractive index material by doping with germanium. For Raman spectroscopy applications, the use of most available polymeric materials as an outer cladding to confine the Raman shifted light should be avoided since these materials typically contribute a Raman or fluorescence spectral signature that confounds the signal from the sample of interest. However, polymeric materials that lack strong Raman signatures in the wavenumber region of interest, such as fluoropolymers, e.g. polytetrafluoroethylene (PTFE, Teflon™), may advantageously be used as an outer cladding in the various embodiments of the invention. The fluoropolymer may, for example, not contain carbon-hydrogen bonds. The fluoropolymer may, for example, be an amorphous fluoropolymer. Chlorotrifluoroethylene homopolymer (CTFE) may, for example, also be used as an outer cladding material. A silica outer cladding may, for example, also be used to confine the collected Raman scattered light in the outer multimode waveguide region. Air clad fibers, also known as holey or photonic bandgap fibers, may also be used to construct the outer multimode waveguide.

Implementation of the HW Raman & OCT combination system

The laser source(s) for HW Raman may be of any suitable kind for the Raman excitation. Excitation light for the HW Raman catheter system may be generated by a semiconductor laser and routed into the catheter fiber(s). Any suitable laser source(s) may be used including without limitation diode-pumped solid state lasers (DPSS). Volume Bragg Grating (VBG) stabilized multi-mode laser diode sources, such as those available from PD-LD, Inc. (Pennington, N.J.) may also be used. The laser source used may be a single mode laser or a multi-mode laser, such as those known in the art. Before being launched into the catheter optical fiber(s), the light may be routed through an optical bandpass filter to provide a spectrally pure excitation source, i.e., without unwanted spectral features that may interfere with the Raman shifted light or that may produce additional unwanted spectral signatures. The light may also be passed through a chromatic beam splitter, where the excitation light is routed into the fiber and then the return light, which has been shifted in wavelength, is routed along another optical path. The laser emission wavelength used for HW Raman spectroscopy may, for example, be in the near-infrared range, be in the range of near-infrared to 2 µm, or be in the range of near-infrared to 1 µm.

In the double-clad fiber, the Raman excitation light will be launched into and guided by the inner core and/or inner clad within the catheter fiber to the region of interest in an artery. Raman-scattered light will be collected at the catheter tip, and the return light will be guided down mostly the outer core of the fiber, but collected light may also reside in the inner core. The returning Rayleigh scattered light, which is at the same wavelength as the excitation wavelength, will preferably be removed from the return beam before it enters the/a spectrometer, which may be accomplished using an optical long-pass filter. The light will then be dispersed chromatically in the spectrometer onto a detection array.

Time domain OCT may be performed with light pulses generated from a mode-locked laser light source. The spectral bandwidth of the light is related to the pulse duration. To increase the spatial resolution of an OCT system, one prefers to utilize short pulses with broad spectral bandwidths, but excitation with broad bandwidth light will limit the spectral resolution of the detected Raman signal. According to the invention, this additional challenge to integrating the two technologies can be addressed by either temporally cycling between the two measurement modalities or compromising the Raman and OCT resolutions to perform simultaneous measurements. Other types of interferometry light sources include broadband light sources such as light-emitting diodes (LEDs), for example, super-luminescent white light LEDs. As mentioned above, the interferometry light source for frequency domain OCT (FD-OCT) will be different and may be a frequency-swept single-mode laser light source.

If the two measurements (HW Raman and OCT) are separated temporally, optical switches may be utilized to cycle between the excitation sources and the return beam paths to accomplish both objectives, i.e., obtain Raman and OCT measurements with the same catheter. A rapid acquisition speed allows both navigation and identification information to be obtained about the same location in the artery. A switching speed in the range of 30 to 50 milliseconds provides a sufficient data acquisition speed for most applications, although other switching time ranges are acceptable. The optical switches used in various embodiments of the invention may be of any suitable kind. For example, bulk optical approaches such as electrical relay-controlled prisms may be used. Acousto-optical switches may be used and permit nanosecond scale switching speeds, Acousto-optical switching is disclosed, for example in U.S. Pat. No. 6,922,498. Microelectromechanical system-based (MEMS) optical switches may also be used, such as those involving the positioning of micro-mirrors and are disclosed, for example, in U.S. Pat. No. 6,396,976. Bubble-based optical switching mechanisms that involve the intersection of two waveguides so that light is deflected from one to the other when an inkjet-like bubble is created may also be used and are disclosed, for example, in U.S. Pat. No. 6,212,308. Electro-optical switches of various types may also be used. One type of electro-optical switch employs the electro-optical effect of some materials in which the index of refraction changes under the influence of an applied electrical field. Such materials include lithium niobate, electro-optical ceramics, polymers and other nonlinear optical and semiconductor materials. The materials may be incorporated into an arm of an interferometer to control the propagation direction of light. Fast switching times can be obtained with electro-optical switches, on the order of nanoseconds for lithium niobate. Operation and coordination of the various switches of embodiments of the invention and for the various modes of operation thereof may be under the control of one or more microprocessors and/or control circuits.

For simultaneous measurements, the same source may be utilized to perform both measurements. Although there may be a tradeoff between OCT spatial resolution and Raman spectral resolution, the simultaneous OCT/Raman spectroscopy modality is highly desirable. For simultaneous measurements, spatial filtering of the collected Raman signals from the OCT return signal may be provided by imaging the fiber face, for example, with great magnification, and employing mechanical apertures to route the Raman signal in the inner cladding (outer core) to the spectrometer system and the inner core light to the OCT analysis system. In one embodiment of simultaneous OCT/Raman spectroscopy according the invention the same light source and/or wavelength range is used for both the OCT and Raman spectroscopy.

The suitable range of excitation wavelength with respect to the Raman spectroscopy aspect of the invention may, for example, be selected so that Raman-shifted light within an area of interest falls within the detection range of the detector device, such as a silicon CCD for wavelengths <~1 micrometer or infrared focal plane array detectors for longer wavelengths in the infrared, that is used to measure the Raman shifted light. In one embodiment, the excitation light wavelength range may be within the wavelength range of long-wavelength visible light to at or about 2 micron. In one embodiment, the excitation light wavelength range may be within the wavelength range of long-wavelength visible light to at or about 1 micron.

A combination Raman and OCT fiber catheter may, for example, be employed in intravascular application with contact configurations, where the sensor touches or very closely nears the arterial wall, or in a rotating catheter configuration, where the fiber probe is rotated around the axis of an artery to obtain a full circumferential mapping of the artery.

FIG. 6. schematically illustrates (not to scale) a side-viewing HW Raman and OCT optical fiber probe embodiment of the invention. The probe includes a double-clad fiber having a core 601, an inner clad 602, an outer clad 603 and a jacket 604. The distal end of the fiber 605 is angle-polished to that light from within the fiber may be directed off-axis to a sample and off-axis light from a sample may be collected into the fiber. Illumination 606 for both Raman spectroscopy and OCT is directed down core 601 and is directed off-axis by distal end 605 (redirected light shown as 607) toward a sample. A first part of the light 608 returning from a sample is directed into the fiber by distal end 605 and travels in core 601 toward the proximal end of the fiber (609) for OCT analysis, for example, by a Michelson interferometer (not shown). A second part of the light 610 is directed into the fiber by distal end 605 and travels in inner clad 602 toward the proximal end of the fiber (611) for Raman spectroscopic analysis by a Raman spectrometer (not shown).

One embodiment of the invention provides a fiber optic probe system configured to perform high wavenumber Raman spectroscopy and optical coherence tomography over an optical fiber that includes: a double clad optical fiber having a proximal end, a distal probe end and a central longitudinal axis and comprising a core, an inner clad surrounding the core and an outer clad surrounding the inner clad, the distal probe end of the fiber being angled to provide off-axis transmission and receipt of light; a laser light source, such as a narrowband laser light source, operably coupled or selectively operably coupleable (for example by operation of a switch) to the proximal end of the double clad fiber to transmit Raman excitation light down the core and/or inner clad of the double clad fiber; a interferometry light source operably coupled or selectively operably coupleable (for example by operation of a switch) to the proximal end of the double clad fiber to transmit light for interferometry down the core of the double clad fiber; a Raman spectrometer operably coupled or selectively operably coupleable (for example by operation of a switch) to the proximal end of the double clad fiber to receive Raman scattered light from a sample via the inner clad of the fiber, said spectrometer configured to measure Raman scattered light in the range of 2,500-4,000 $cm^{-1}$; and an interferometer operably coupled or selectively operably coupleable (for example by operation of a switch) to the proximal end of the double clad fiber to receive phase-shifted light from a sample via the core of the fiber; and The system may further include an optical switch configured to switch between providing illumination by the laser light source for Raman spectroscopy and the interferometry light source for interferometry.

Another embodiment of the invention provides a basket catheter optical probe system configured for performing high wavenumber Raman spectroscopy and optical coherence tomography over an optical fiber that includes: an elongate basket catheter body comprising a proximal end and a distal end, and at or near the distal end a basket section comprising wall-approaching (or contacting) probe arms; a double clad optical fiber having a proximal end, a distal probe end and a central longitudinal axis and comprising a core, an inner clad surrounding the core and an outer clad surrounding the inner clad, the distal probe end of the fiber being angled to provide off-axis transmission and receipt of light, said double clad fiber being extending within the elongate basket catheter body, the distal probe end of the double clad fiber terminating within a wall-approaching (or contacting) probe arm of the catheter; a laser light source operably coupled or selectively operably coupleable to the proximal end of the double clad fiber to transmit Raman excitation light down the core and/or inner clad of the double clad fiber; a interferometry light source operably coupled or selectively operably coupleable to the proximal end of the double clad fiber to transmit light for interferometry down the core of the double clad fiber; a Raman spectrometer operably coupled or selectively operably coupleable to the proximal end of the double clad fiber to receive Raman scattered light from a sample via the inner clad of the fiber, said spectrometer configured to measure Raman scattered light in the range of 2,500-4,000 $cm^{-1}$; and an interferometer operably coupled or selectively operably coupleable to the proximal end of the double clad fiber to receive phase-shifted light from a sample via the core of the fiber. The system may further include an optical switch configured to switch between providing illumination by the laser light source for Raman spectroscopy and the interferometry light source for interferometry.

More generally, in a related embodiment, one or more double clad optical fiber probes of the invention may be incorporated into any type of catheter or intravascular catheter having lumen wall-approaching (or contacting) probes. For example, in a basket catheter having 2, 3, 4, 5, 6, or more probe arms (basket splines) one or more or all of the arms may have an optical fiber probe terminate in or near the wall-contacting portion of a probe arm and which are oriented so that their field-of-field looks radially outward (toward the wall of the vessel or lumen). Basket type catheter designs as well as other types of catheter designs having wall-contacting probes that may be readily adapted to the present invention include, for example, those disclosed in U.S. Publication No. 2004/0260182, which is incorporated herein by reference.

Figure 7:
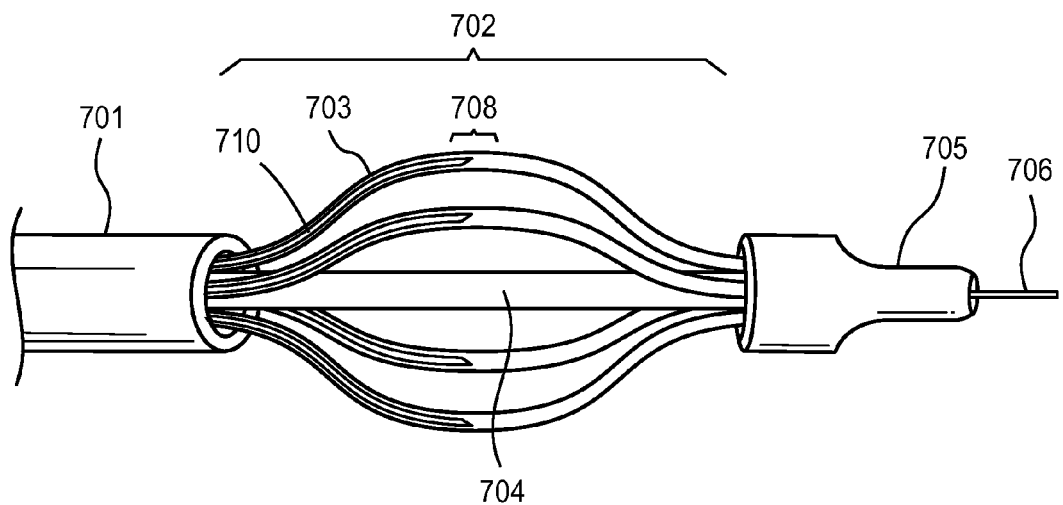
FIG. 7 shows a basket catheter embodiment of the invention.

FIG. 7 shows a basket-style side-viewing optical catheter embodiment of the invention that has a proximal outer shaft 701, a basket section 702 including four probe arms 703 each including one or more side viewing optical fibers 710 (or side-viewing optical assemblies of a fiber and a beam redirecting element), that terminate in or around the apex of the radially extended probe arm (side-viewing portion 708 of the basket section) in order to contact or near a vessel wall so that Raman spectroscopic and interferometric evaluations of a lumen wall, such as a blood vessel wall, can be performed. The catheter also includes a distal tip 705 that is connected to a guidewire tube 704, so that the catheter may travel over a guidewire 706, and to the distal end of each probe arm. The viewing portion of the probe arms may have a window to permit direct viewing by the side-viewing portions of the optical fiber (or the optical assembly of a fiber and a beam redirecting element). Radial expansion and contraction of the probe arms of the basket section may be accomplished by contracting and extending the opposite ends of the probe arms, respectively. The guidewire tube, which is attached to the distal tip of the catheter, may for example, be slideable within the catheter thereby permitting said contracting and extending of the opposite ends of the probe with respect to each other, while the proximal ends of the probe arms remain fixed with respect to the proximal outer shaft. Alternatively, for example, a slideable sheath may be provided to control the radial extension of the basket section. Optional radiopaque marker bands may also be provided to aid in visualizing the catheter within a blood vessel. The basket catheter may, for example, be an intravascular catheter sized for use in human coronary and/or carotid arteries.

The invention also provides side-viewing probe embodiments in which the probe fiber itself or a shaft including the probe fiber(s) of the invention rotates to provide a radial scan or in which a beam redirecting element (such a mirror or prism) in optical communication with the probe fiber of the invention rotates to provide radial scanning. Rotational mechanisms for obtaining radial scans are well known in the art. Accordingly, one embodiment of the invention provides a catheter, such as an intravascular catheter, which may be sized for use in the human coronary and/or carotid arteries, that includes a side-viewing optical fiber (or side-viewing assembly of a fiber and beam redirecting element) according to the invention, wherein the catheter is configured to provide rotation of the fiber in order to provide radial scanning or is configured to rotate a beam redirecting element (such a mirror or prism) in optical communication with the probe fiber of the invention rotates to provide radial scanning.

Front-looking or at least partially front-looking optical fiber probes are also provided by and within the scope of the invention. In this case, the distal tip of the double clad optical fiber will not be angled to provide lateral viewing. The front-viewing configuration is well suited to intravascular catheter designs in which the distal end of an elongate wall-contacting probe is extended from the side of the catheter to contact a tissue target in a "head-on" manner.

A related embodiment of the invention provides a method for optically analyzing a blood vessel that includes the steps of: inserting into a blood vessel a double clad optical fiber having a proximal end, a distal probe end and a central longitudinal axis and comprising a core, an inner clad surrounding the core and an outer clad surrounding the inner clad, the distal probe end of the fiber being angled to provide off-axis transmission and receipt of light; launching laser light into the core and/or inner clad of the double clad fiber at its proximal end to illuminate a tissue region via the distal end of the double clad fiber, thereby generating a Raman spectra from the tissue region; receiving the Raman spectra via the inner clad of the fiber at the proximal end of the double clad fiber, and measuring the Raman spectra in the range 2,500-4,000 cm$^{-1}$ using a Raman spectrometer configured to measure said range; launching light from an interferometry light source into the core of the double clad fiber at its proximal end to illuminate the tissue region via the distal end of the double clad fiber, thereby producing a sample beam for interferometric analysis; receiving the sample beam via the core of the double clad fiber at its proximal end and performing interferometry by combining the sample beam with a reference beam using an interferometer, thereby obtaining both Raman spectroscopic data and interferometric data for the tissue region.

The method may, for example, include repeatedly switching between (i.) providing illumination from the laser light source and measuring the Raman spectra and (ii.) providing illumination from the interferometry light source and performing interferometry. Still further, the method may include the step of longitudinally displacing the distal probe end in a blood vessel, such as an artery, while rapidly performing the switching between the two optical interrogation modalities. Where the double clad fiber probe is presented within a catheter such as an intravascular catheter, a mechanical pullback mechanism may be used to perform said longitudinal displacement. The method may also include a step of disposing the distal probe end of the double clad fiber to contact or be in close proximity to the tissue region target in any suitable manner.

In any of the above embodiments, the interferometer may, for example, be a Michelson interferometer. In any of the above embodiments, the laser light source may emit (or the laser light may be emitted) at a wavelength at or about 671 nm for performing the HW Raman spectroscopy, such as a Model RCL-100-671 100 mW, 671 nm, TEMoo, DPSS, CW laser with power supply from CrystaLaser (Reno, Nev., USA). In any of the above embodiments, measurement may, for example, optionally be restricted to an even narrower region within the HW Raman region such as for example, the range of 2,500-3,700 cm$^{-1}$ or the range of 2,600 to 3,200 cm$^{-1}$. Any of the systems of the invention may further include at least one microprocessor and/or control circuitry to control the operation of the components of the system and/or to analyze the data obtained using the systems. Generally, the at least one microprocessor may be provided with computer accessible memory and computer instructions directing the processor to carry out various operations.

Each of the patents and other publications cited in this disclosure is incorporated by reference in its entirety.

While certain embodiments of the invention are exemplified herein with respect to the optical analysis of tissue, it should be understood that the optical fibers, probe embodiments and systems (apparatuses) of the invention are not limited to use in particular applications or types of samples, except as may be explicitly indicated herein.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A fiber optic probe system capable of performing high wavenumber Raman spectroscopy and optical coherence tomography over an optical fiber, comprising:
   a double clad optical fiber having a proximal end, a distal probe end and a central longitudinal axis and comprising a core, an inner clad surrounding the core and an outer clad surrounding the inner clad;
   a laser light source operably coupled or selectively operably coupleable to the proximal end of the double clad fiber to transmit Raman excitation light down at least one of the core and the inner clad of the double clad fiber;

an interferometry light source operably coupled or selectively operably coupleable to the proximal end of the double clad fiber to transmit light down the core of the double clad fiber;

a Raman spectrometer operably coupled or selectively operably coupleable to the proximal end of the double clad fiber to receive Raman scattered light from a sample via the inner clad of the fiber, said spectrometer configured to measure Raman scattered light in the range of 2,500-4,000 cm$^{-1}$; and an interferometer operably coupled or selectively operably coupleable to the proximal end of the double clad fiber to receive phase-shifted light from a sample via the core of the fiber and combine the phase-shifted light with a reference beam.

2. The system of claim 1, wherein the interferometer is a Michelson interferometer.

3. The system of claim 1, wherein the laser light source emits light in the near-infrared wavelength range.

4. The system of claim 3, wherein the laser light source emits light in the wavelength range of near-infrared visible light to 2 μm.

5. The system of claim 1, wherein the outer clad is made from a fluoropolymer.

6. The system of claim 1, wherein a fiber Bragg grating filter is inscribed in the core of the fiber to at least partially filter out Raman background light arising from the core of the fiber.

7. The system of claim 6, wherein the fiber Bragg grating filter is inscribed at an angle to the longitudinal axis of the fiber in order to direct the Raman background light off-axis (out of the fiber).

8. The system of claim 1, further comprising an optical switch configured to switch between providing illumination by the laser light source for Raman spectroscopy and the interferometry light source for interferometry.

9. The system of claim 1, wherein the system is configured to simultaneously collect the Raman scattered light and the phase-shifted light.

10. A basket catheter optical probe system capable of performing high wavenumber Raman spectroscopy and optical coherence tomography over an optical fiber:

an elongate basket catheter body comprising a proximal end and a distal end, and at or near the distal end a basket section comprising wall-approaching probe arms;

a double clad optical fiber having a proximal end, a distal probe end and a central longitudinal axis and comprising a core, an inner clad surrounding the core and an outer clad surrounding the inner clad, said double clad fiber extending within the elongate basket catheter body, the distal probe end of the double clad fiber terminating within a wall approaching probe arm of the catheter;

a laser light source operably coupled or selectively operably coupleable to the proximal end of the double clad fiber to transmit Raman excitation light down at least one of the core and the inner clad of the double clad fiber;

an interferometry light source operably coupled or selectively operably coupleable to the proximal end of the double clad fiber to transmit light from the interferometry light source down the core of the double clad fiber;

a Raman spectrometer operably coupled or selectively operably coupleable to the proximal end of the double clad fiber to receive Raman scattered light from a sample via the inner clad of the fiber, said spectrometer configured to measure Raman scattered light in the range of 2,500-4,000 cm$^{-1}$; and an interferometer operably coupled or selectively operably coupleable to the proximal end of the double clad fiber to receive phase-shifted light from a sample via the core of the fiber.

11. The system of claim 10, wherein the interferometer is a Michelson interferometer.

12. The system of claim 10, wherein the laser light source emits light in the near-infrared wavelength range.

13. The system of claim 12, wherein the laser light source emits light in the wavelength range of near-infrared visible light to 2 μm.

14. The system of claim 10, wherein the outer clad is made from a fluoropolymer.

15. The system of claim 10, wherein a fiber Bragg grating filter is inscribed in at least one of the core and the inner clad of the fiber to at least partially filter out Raman background light.

16. The system of claim 15, wherein the fiber Bragg grating filter is inscribed at an angle to the longitudinal axis of the fiber in order to direct the Raman background.

17. The system of claim 10, further comprising an optical switch configured to switch between providing illumination by the laser light source for Raman spectroscopy and the interferometry light source for interferometry.

18. The system of claim 10, wherein the system is configured to perform simultaneous Raman spectroscopy and interferometry.

19. A method for optically analyzing a blood vessel, comprising the steps of:

inserting into a blood vessel a double clad optical fiber having a proximal end, a distal probe end and a central longitudinal axis and comprising a core, an inner clad surrounding the core and an outer clad surrounding the inner clad;

launching laser light into at least one of the core and the inner clad of the double clad fiber at its proximal end to illuminate a tissue region via the distal end of the double clad fiber, thereby generating a Raman spectra from the tissue region;

receiving the Raman spectra via the inner clad of the fiber at the proximal end of the double clad fiber, and measuring the Raman spectra in the range 2,500-4,000 cm$^{-1}$ using a Raman spectrometer configured to measure said range;

launching light from an interferometry light source into the core of the double clad fiber at its proximal end to illuminate the tissue region via the distal end of the double clad fiber, thereby producing a sample beam for interferometric analysis;

receiving the sample beam via the core of the double clad fiber at its proximal end and performing interferometer by combining the sample beam with a reference beam using an interferometer, thereby obtaining both Raman spectroscopic data and interferometric data for the tissue region.

20. The method of claim 19, wherein the interferometer is a Michelson interferometer.

21. The method of claim 19, wherein the laser light source emits light in the near-infrared wavelength range.

22. The method of claim 21, wherein the laser light source emits light in the wavelength range of near-infrared visible light to 2 μm.

23. The method of claim 19, wherein the outer clad is made from a fluoropolymer.

24. The method of claim 19, wherein a fiber Bragg grating filter is inscribed in at least one of the core and the inner clad of the fiber to at least partially filter out Raman background light.

25. The method of claim 24, wherein the fiber Bragg grating filter is inscribed at an angle to the longitudinal axis of the fiber in order to direct the Raman background light off-axis (out of the fiber).

26. The method of claim 19, wherein the method comprises repeatedly switching between (i.) providing illumination from the laser light source and measuring the Raman spectra and (ii.) providing illumination from the interferometry light source and performing interferometry.

27. The method of claim 19, wherein the method comprises simultaneously receiving Raman-scattered light and phase-shifted light from the tissue region.

28. A method for optically analyzing a blood vessel, comprising the steps of:
   inserting into a blood vessel a double clad optical fiber having a proximal end, a distal probe end and a central longitudinal axis and comprising a core, an inner clad surrounding the core and an outer clad surrounding the inner clad;
   launching light having a wavelength range into at least one of the core and the inner clad of the double clad fiber at its proximal end to illuminate a tissue region via the distal end of the double clad fiber, thereby generating both Raman-scattered light from the tissue region and phase shifted light from the tissue region;
   receiving the Raman-scattered light via the inner clad of the fiber at the proximal end of the double clad fiber, and measuring the Raman-scattered light using a Raman spectrometer configured;
   receiving the phase-shifted light via the core of the double clad fiber at its proximal end and performing interferometry by combining the phase-shifted with a reference beam using an interferometer,
   thereby obtaining both Raman spectroscopic data and interferometric data for the tissue region.

29. The method of claim 28, wherein the Raman spectrometer configured to measure Raman scattered light in the range of 2,500-4,000 $cm^{-1}$.

30. The method of claim 28, wherein the interferometer is a Michelson interferometer.

31. The method of claim 28, wherein the outer clad is made from a fluoropolymer.

32. The method of claim 28, wherein a fiber Bragg grating filter is inscribed in at least one of the core and the inner clad of the fiber to at least partially filter out Raman background light.

33. The method of claim 32, wherein the fiber Bragg grating filter is inscribed at an angle to the longitudinal axis of the fiber in order to direct the Raman background light off-axis (out of the fiber).

34. The method of claim 28, wherein the method comprises simultaneously receiving Raman-scattered light and phase-shifted light from the tissue region.

* * * * *